(12) United States Patent
Tsujita

(10) Patent No.: US 7,349,725 B2
(45) Date of Patent: Mar. 25, 2008

(54) FLUORESCENT IMAGE OBTAINING APPARATUS

(75) Inventor: Kazuhiro Tsujita, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1336 days.

(21) Appl. No.: 09/888,444

(22) Filed: Jun. 26, 2001

(65) Prior Publication Data

US 2001/0056238 A1   Dec. 27, 2001

(30) Foreign Application Priority Data

Jun. 26, 2000 (JP) ............................. 2000-190701

(51) Int. Cl.
*A61B 5/00* (2006.01)
(52) U.S. Cl. ..................... 600/323; 600/473; 600/476
(58) Field of Classification Search ......... 600/473–478
See application file for complete search history.

(56) References Cited

U.S. PATENT DOCUMENTS

| | | | |
|---|---|---|---|
| 4,422,457 A * | 12/1983 | Hattori ........................ | 606/2 |
| 4,951,135 A | 8/1990 | Sasagawa et al. | |
| 5,106,387 A | 4/1992 | Kittrell et al. | |
| 5,187,572 A | 2/1993 | Nakamura et al. | |
| 5,749,830 A | 5/1998 | Kaneko et al. | |
| 6,070,096 A | 5/2000 | Hayashi | |
| 6,462,770 B1 * | 10/2002 | Cline et al. ................... | 348/65 |
| 6,690,958 B1 * | 2/2004 | Walker et al. ............... | 600/323 |
| 6,975,899 B2 * | 12/2005 | Faupel et al. ............... | 600/476 |

FOREIGN PATENT DOCUMENTS

| | | |
|---|---|---|
| DE | 196 19 734 A1 | 11/1996 |
| EP | 0 920 831 A1 | 6/1999 |
| WO | WO 99/37204 A1 | 7/1999 |
| WO | WO 99/53832 A1 | 10/1999 |
| WO | WO 99/66830 A1 | 12/1999 |
| WO | WO 00/42910 A1 | 7/2000 |

OTHER PUBLICATIONS

Japanese Abstract No. 09173296, dated Jul. 8, 1997.

* cited by examiner

*Primary Examiner*—Brian L. Casler
*Assistant Examiner*—John F. Ramirez
(74) *Attorney, Agent, or Firm*—Sughrue Mion, PLLC

(57) ABSTRACT

A fluorescent-light image obtaining apparatus for obtaining an autofluorescent-light image emitted from a target tissue irradiated by an excitation light, wherein the safety of the patient is ensured against injury from exposure to excessive excitation light when the distance between the output end of the excitation light projector and the target tissue is short. A contact detector detects that the end of the excitation light projector of the endoscope is in contact with the target tissue. Then, an excitation light output controller receives a signal indicating that the end of the excitation light projector is in contact with the target tissue. In response to this signal, the excitation light output controller stops the emission of the excitation light, or reduces the intensity of the emitted excitation light to a safe intensity for the patient even while the end of the excitation light projector and the target tissue are in contact.

17 Claims, 7 Drawing Sheets

F I G. 2
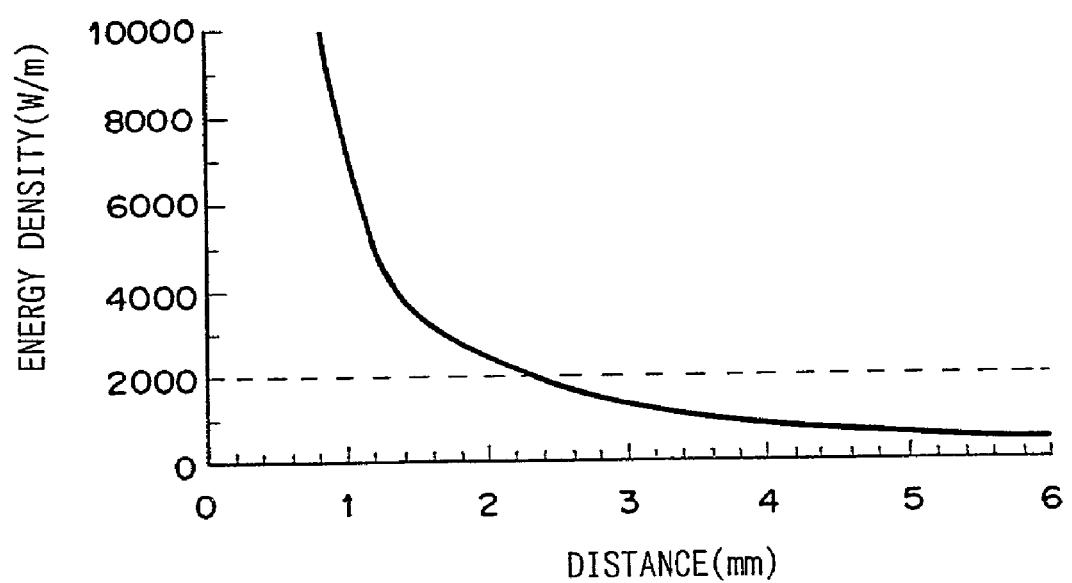

FLUORESCENT IMAGE OBTAINING APPARATUS

BACKGROUND OF THE INVENTION

1. Field of the Invention

The present invention relates to a fluorescent-light image obtaining apparatus for obtaining a fluorescent-light image of the fluorescent-light emitted from a target tissue upon irradiation thereof by an excitation light.

2. Description of the Related Art

There have been proposed technologies for irradiating a target tissue with an excitation light of a wavelength within the wavelength range of the intrinsic tissue fluorophores of the target tissue, and receiving the fluorescent-light emitted from the intrinsic tissue fluorophores of the target tissue thereupon, wherein, utilizing the difference between the fluorescent-light emitted from a normal tissue and the fluorescent-light emitted by a diseased tissue upon irradiation thereof by an excitation light of a predetermined wavelength, a fluorescent-light image of the location of the diseased tissue and its range of lesion is displayed.

Normally, when irradiated by excitation light, as shown by the solid line in FIG. 1, because a strong fluorescent-light is emitted by a normal tissue and a fluorescent-light weaker than that emitted from the normal tissue is emitted from a diseased tissue, as shown by the broken line in the same figure, by measuring the intensity of the fluorescent-light, it can be determined whether the target tissue is in a normal state or a diseased state. However, the fluorescent-light emitted from a target tissue is extremely weak, and because the detection thereof is difficult, as large intensity of fluorescent-light as possible is desirable. However, because there is a fear that injury to the patient result from too strong an excitation light, it must be controlled to be of a uniform intensity below a certain level. Levels of intensity of excitation light that do not cause injury to a patient are defined as MPE values according to the JIS standard, etc. Further, because the excitation light is spread at an angle of 100° at the excitation light emitting end of the endoscope insertion portion, as shown in FIG. 2, the relationship of the distance between the distal end of excitation light emitting means and the target area to the intensity of the excitation light received at the target area is such that the intensity of the excitation light becomes greater as the distance becomes shorter. Accordingly, the distance between the distal end of excitation light emitting means and the target area facilitating operation below the MPE value of 2000 W/m2 shown in FIG. 2 is 3 mm or more.

However, in using a fluorescence endoscope apparatus, etc., because the target tissue is a tube-shaped organ, the excitation light emitting end of the endoscope insertion portion cannot be fixed in place and the distance between the target area an the excitation light emitting end of the endoscope insertion portion is not uniform. Therefore, when the intensity of the excitation light has been set close to the MPE value in order to obtain adequate fluorescent-light, if the distance between the excitation light emitting end of the endoscope insertion portion and the target area becomes less than 3 mm, it is possible for the target tissue of the target area be injured. On the other hand, under all measurement-taking conditions, including cases in which the distance between the excitation light emitting end of the endoscope insertion portion and the target area becomes less than 3 mm, for cases in which the intensity of the excitation light has been set so as to ensure for the safety of the target tissue of the target area, at the far end of the normal operational distance range (50-100 mm), the intensity of the excitation light becomes weak and an adequate intensity of fluorescent-light is not obtained, whereby the accuracy of the detection is reduced. Further, for cases in which the sensitivity of the detection system has been increased in order to detect such weak levels of fluorescent-light, the increase in the cost of the system is extremely high.

SUMMARY OF THE INVENTION

The present invention has been developed in consideration of the circumstances described above, and it is a primary object of the present invention to provide a fluorescent-light image obtaining apparatus in which the safety of the patient is ensured and no deterioration to the detection, or exorbitant increase in the cost of the apparatus is incurred.

A fluorescent-light image obtaining apparatus according to the present invention comprises an excitation light emitting means for projecting excitation light onto a target tissue, an illuminating light emitting means for projecting illuminating light onto the target tissue, a fluorescent-light image obtaining means for obtaining a fluorescent-light image formed of the fluorescent-light emitted from the target tissue upon irradiation thereof by the excitation light, a normal-image obtaining means for obtaining a normal-image formed of the illuminating light reflected from the target tissue upon irradiation thereof by the illuminating light, further comprising a contact detecting means for detecting that the distal end of excitation light emitting means has come into contact with the target tissue, and an excitation light emission controlling means for controlling, in response to the detection signal of the contact detecting means, the output of the excitation light emitted from the excitation light emitting means.

According to the fluorescent-light image obtaining apparatus of the present invention, the contact detecting means detects whether or not the excitation light emitting end of the endoscope insertion portion is in contact with the target tissue. Then, a detection signal indicating that the distal end of excitation light emitting means is in contact with the target tissue is output to an excitation light emission controlling means, which controls, according to the detection signal, the output of the excitation light emitted from the excitation light emitting means.

The excitation light emission controlling means can stop the emission of excitation light from the excitation light emitting means.

In addition, the excitation light emission controlling means can control the intensity of the excitation light output from the excitation light emitting means to be below a predetermined intensity. Here, "predetermined intensity" refers to an excitation light intensity safe to the patient, that is, an intensity of excitation light at which injury is not caused to the target tissue of the target area, even under conditions in which the distal end of excitation light emitting means is in contact with the target tissue.

Another fluorescent-light image obtaining apparatus according to the present invention comprises an excitation light emitting means for projecting excitation light onto a target tissue, an illuminating light emitting means for projecting illuminating light onto the target tissue, a fluorescent-light image obtaining means for obtaining a fluorescent-light image formed of the fluorescent-light emitted from the target tissue upon irradiation thereof by the excitation light, a normal-image obtaining means for obtaining a normal-image formed of the illuminating light reflected from the target tissue upon irradiation thereof by the illuminating light, further comprising a distance parameter detecting means for detecting a parameter correlating the distance between the distal end of excitation light emitting means and the target tissue, and an excitation light emission controlling means for controlling, based on the distance parameter of the contact detecting means, the output of the excitation light emitted from the excitation light emitting means.

According to the fluorescent-light image obtaining apparatus of the present invention, the distance parameter detecting means detects whether or not the excitation light emitting end of the endoscope insertion portion is in contact with the target tissue. Then, the detected distance parameter is output to an excitation light emission controlling means, which controls, according to the detected distance parameter, the output of the excitation light emitted from the excitation light emitting means.

Aforementioned parameter can be based on the light intensity of a fluorescent-light image photographed by the fluorescent-light image obtaining means. Here, for example, the excitation light emission controlling means computes, based on the detected light intensity of the fluorescent-light image detected by the distance parameter detecting means, the percentage of the entire image or a portion of a specified image occupied by pixels of a size larger than a predetermined threshold value. Then, when this percentage is above a predetermined threshold value, the excitation light emission controlling means can control the output of the excitation light.

Further, the peak measured light value (the largest value of the pixel values) can be obtained for the entire fluorescent-light image or a specified portion thereof, and when this value is larger than a predetermined threshold value, the output of the excitation light from the excitation light emitting means can be controlled.

Instead, aforementioned parameter can be based on the light intensity of a normal image photographed by the normal-image obtaining means. Here, for example, the excitation light emission controlling means computes, based on the detected light intensity of the normal image detected by the distance parameter detecting means, the percentage of the entire image or a portion of a specified image occupied by pixels of a size larger than a predetermined threshold value. Then, when this percentage is above a predetermined threshold value, the excitation light emission controlling means can control the output of the excitation light.

Further, the peak measured light value (the largest value of the pixel values) can be obtained for the entire normal-image or a specified portion thereof, and when this value is larger than a predetermined threshold value, the output of the excitation light from the excitation light emitting means can be controlled.

In addition, yet another fluorescent-light image obtaining apparatus according to the present invention comprises a reference light emitting means for projecting reference light onto a target tissue, and a reflected-image obtaining means for obtaining a reflected-image formed of the reference light reflected from the target tissue upon irradiation thereof by the reference light, wherein the parameter detected by the distance parameter detecting means can be based on the light intensity of the reflected-image. Here, the excitation light emission controlling means computes, based on the detected light intensity of the reflected-image detected by the distance parameter detecting means, the percentage of the entire image or a portion of a specified image occupied by pixels of a size larger than a predetermined threshold value. Then, when this percentage is above a predetermined threshold value, the excitation light emission controlling means can control the output of the excitation light.

Further, the peak measured light value (the largest value of the pixel values) can be obtained for the entire reflected-light image or a specified portion thereof, and when this value is larger than a predetermined threshold value, the output of the excitation light from the excitation light emitting means can be controlled.

Still further, the excitation light emission controlling means can be a current controlling means for controlling the current of the excitation light source of the excitation light emitting means.

The excitation light emission controlling means can stop the emission of excitation light from the excitation light emitting means.

Further, the excitation light emission controlling means can control the intensity of the excitation light output from the excitation light emitting means to be below a predetermined intensity. Here, "predetermined intensity" refers to a light intensity safe to the patient; that is, an excitation light intensity not causing injury to the target tissue when the distance between the excitation light emitting end of the endoscope insertion portion and the target tissue is set at a certain distance satisfying the aforementioned threshold value conditions.

According to fluorescent-light image obtaining apparatus of the configuration described above according to the present invention, that the target tissue and the excitation light emitting end of the endoscope insertion portion have come in contact is detected, and the emission of the excitation light from the excitation light emitting means can be stopped in response to this signal, or controlled so as to be of an intensity that, even while the end of the excitation light projector and the target tissue are in contact, does not cause injury to the target tissue, whereby the safety of the patient can be ensured.

In addition, according to fluorescent-light image obtaining apparatus of the configuration described above according to the present invention, a parameter correlating the distance between the excitation light emitting end of the endoscope insertion portion and the target tissue is detected, and the emission of the excitation light from the excitation light emitting means is stopped in response to this signal, or controlled so as to be of an intensity that, even while the end of the excitation light projector and the target tissue are in contact, does not cause injury to the target tissue, whereby the safety of the patient can be ensured.

Further, aforementioned parameter can be based on the light intensity of a fluorescent-light image, a normal-image, or a reflected-light image, whereby the configuration of the apparatus can be kept simple and the cost kept down.

Still further, according to the fluorescent-light image obtaining apparatus of the present invention, the light intensity of a fluorescent-light image, a normal image or a reflected-image, that is, the percentage of an entire image or of a portion of an image occupied by pixels having a pixel value larger than a predetermined threshold value is computed. When this percentage is above a predetermined threshold value, the excitation light emitted from the excitation light emitting means can be stopped or controlled so as to be of a light intensity safe to the patient, that is, an excitation light intensity not causing injury to the target tissue when the distance between the excitation light emitting end of the endoscope insertion portion and the target tissue is set at a certain distance satisfying the aforementioned threshold value conditions. Further, by selecting an appropriate threshold value, the safety of the patient can be ensured with a higher degree of reliability.

In addition, by performing control of the output of the excitation light, such as that described above, deterioration of the degree of accuracy of detection or increase in cost is not incurred, and the safety of the patient can be ensured.

Further, for cases in which the peak measured light value (the largest value of the pixel values) is obtained for the entire reflected-light image or a specified portion thereof, and the output of the excitation light from the excitation light emitting means is controlled when this value is larger than a predetermined threshold value, because only a peak value holding circuit needs to be provided, control of the emission of the excitation light of the can be carried out by an even further simplified configuration.

Still further, for cases in which the target tissue is a tube-shaped organ, if the peak measured light value, etc. is obtained of the specified circumference portion of fluorescent-light image, a reflected-light image, or a normal-image, control of the emission of excitation light can be performed such that the distance is more accurately reflected.

BRIEF DESCRIPTION OF THE DRAWINGS

FIG. 2 shows the energy density of the excitation light received at the target area relative to the distance between the excitation light emitting end of the endoscope insertion portion and the target area.

DESCRIPTION OF THE PREFERRED EMBODIMENTS

Figure 1:
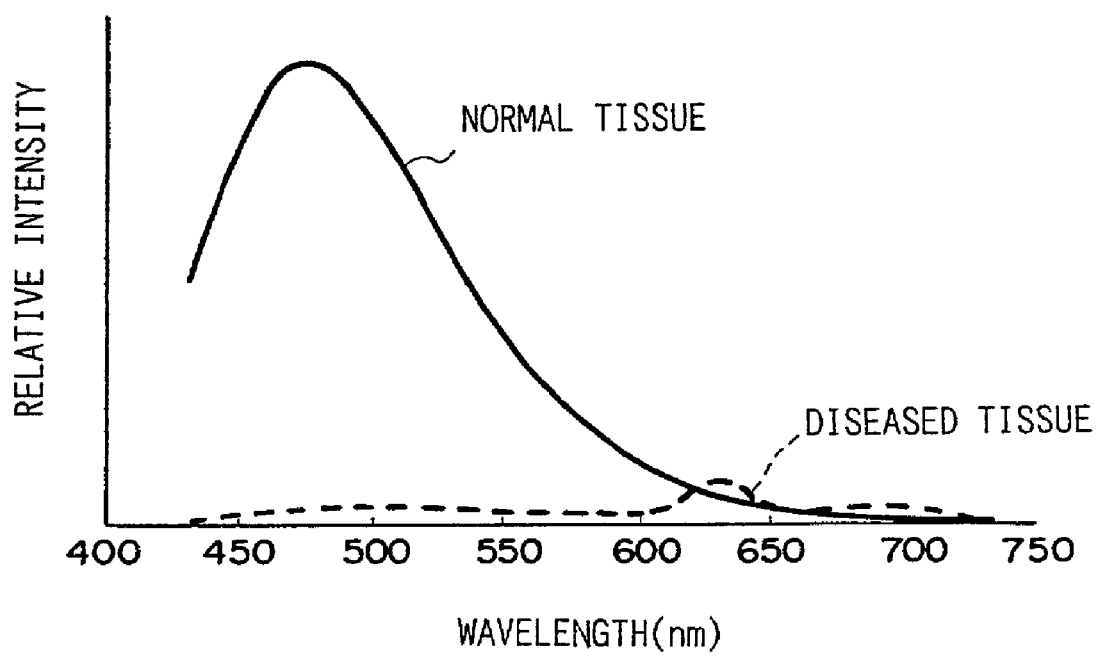
FIG. 1 is a drawing provided for explanation of the distribution of the intensity of the fluorescence spectra in an autofluorescent-light image.
Figure 3:
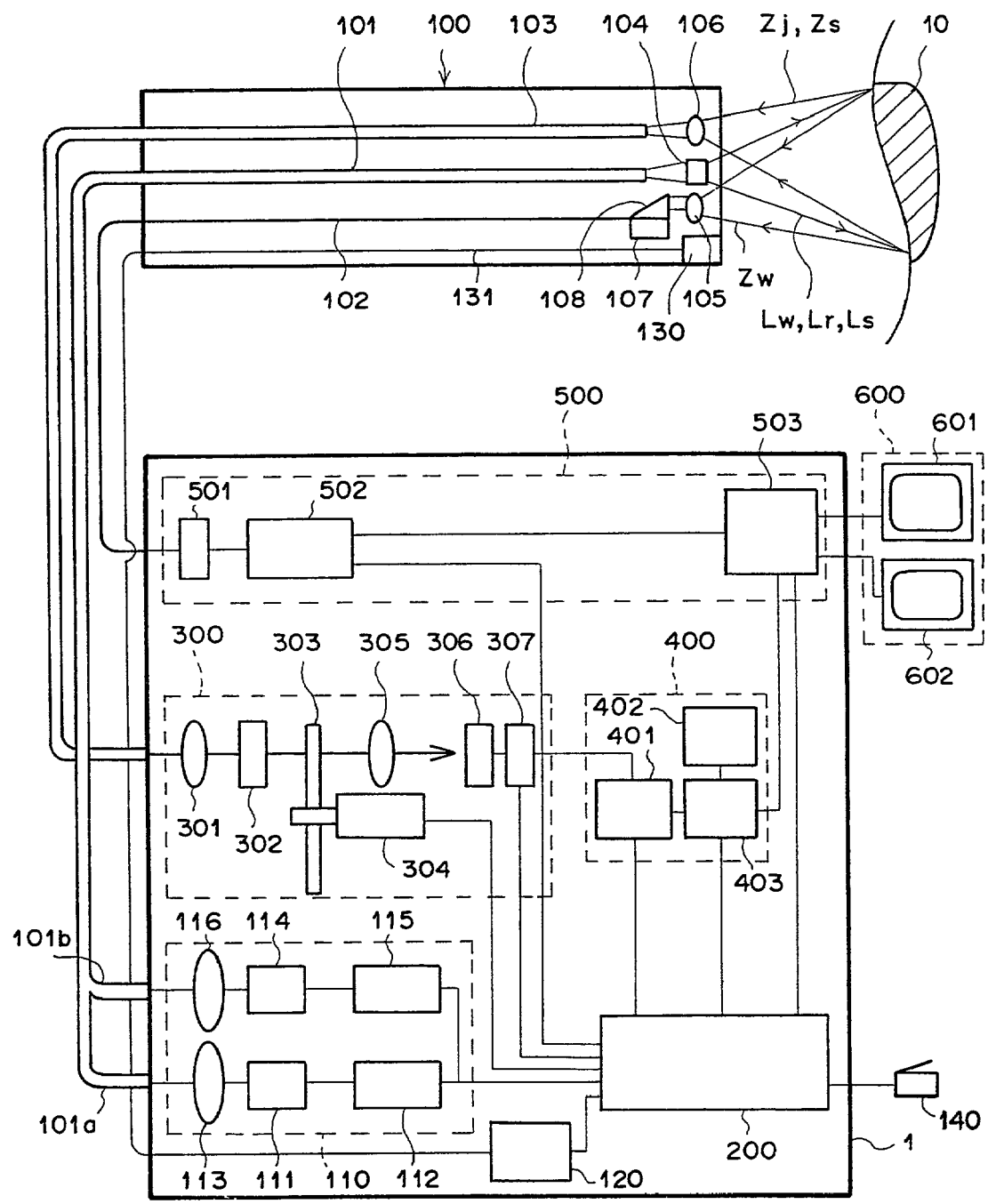
FIG. 3 is a schematic drawing of a fluorescence endoscope apparatus according to the first embodiment of the present invention.

Hereinafter, with reference to the drawings, the preferred embodiments of the present invention will be explained. FIG. 3 is a schematic drawing of a fluorescence endoscope apparatus implementing the fluorescent-light image display apparatus according to the present invention.

The fluorescence endoscope apparatus according to the first embodiment of the present invention comprises: an image signal processing portion 1 provided with an endoscope insertion portion 100 to be inserted into the body of the patient to the position at which the primary nidus of a disease and areas of suspected secondary infection are located, an illuminating unit 110 provided with 2 light sources, one for emitting normal-image use white-light Lw and one for emitting autofluorescent-light image use excitation light Lr, an image detecting unit 300 for obtaining an autofluorescent-light image Zj of the autofluorescent-light emitted from a target tissue 10 upon irradiation thereof by the excitation light Lr, and digitizing and outputting said autofluorescent-light image Zj as two-dimensional digital data, an image computing unit 400 for computing a distance correction value, etc. from the two-dimensional data output from the image detecting unit 300 and computing a computed-image, and comparing the data of each pixel to prerecorded standards values and outputting a signal based on the results of said comparison, a display signal processing means 500 for digitizing a normal-image and obtaining a two-dimensional data thereof, and converting said two-dimensional data and the signal output from the image computing unit 400 to a video signal and outputting said video signal, an excitation light emission controlling means 120 for controlling, in response to a detection signal that the excitation light emitting end of the endoscope insertion portion 100 and the target tissue 10 are in contact, the output of the excitation light, a control computer 200, which is connected to each of the units, for controlling the operation timing thereof; a monitor 600 for displaying as a visible image the signal processed by the display-signal processing unit 500, and a foot-switch 140 for initiating emission of the excitation light.

The endoscope insertion portion 100 comprises a light guide 101 extending to the forward end in the internal portion, a CCD cable 102, an image fiber 103, and a detection signal line 131. The forward end portion of the light guide 101 and the CCD cable 102, that is, the forward end portion of the endoscope insertion portion 100, is provided with an illuminating lens 104 and an objective lens 105. Further, the image fiber 103 is a silicon glass fiber, and a focusing lens 106 is provided at the forward end thereof. A normal-image use detecting element 107 is connected to the forward end of the CCD cable 102, and a reflection-use prism 108 is attached to said normal-image use detecting element 107. The light guide 101 is an integrated cable in which a white-light 101a formed of composite glass fiber and an excitation light guide 101b formed of silicon glass fiber are bundled, and the white-light guide 101a and the excitation light guide 101b are connected to the illuminating unit 110. One end of the CCD cable 102 is connected to the display signal processing unit 140. One end of the image fiber 103 is connected to the image detecting unit 300, and one end of the detection signal line is connected to the excitation light emission controlling means 120.

The illuminating unit 110 comprises: a white-light source 111 for emitting normal-image use white-light Lw and a white-light use power source 112 electrically connected to said white-light source 111, and a white-light use focusing lens 113 for focusing the white light emitted from the white-light source; a GaN semiconductor laser 114 for emitting fluorescent-light image obtaining-use excitation light L2 and a semiconductor-laser use power source 115 electrically connected to said GaN semiconductor laser 114, and an excitation light use focusing lens 116 for focusing the excitation light emitted from the GaN semiconductor laser 114.

The image detecting unit 300 is connected to an image fiber 103, and comprises a fluorescent-light use collimator lens 301 for guiding to a focusing system an autofluorescent-light image Zj conveyed through the image fiber 103, an excitation light cutoff filter 302 for cutting off from the autofluorescent-light image light having a wavelength near that of the excitation light, an optical transmitting filter 303 for extracting a desired wavelength band from the autofluorescent-light image transmitted by the cutoff filter 302, a filter rotating apparatus 304 for rotating the optical transmitting filter 303, a fluorescent-light use focusing lens 305 for focusing the autofluorescent-light image Zj transmitted by the optical transmitting filter 303, a high-sensitivity fluorescent-light image use detecting element 306 for obtaining the autofluorescent-light image Zj focused by the focusing lens 305, and an A/D converter 307 for digitizing the autofluorescent-light image Zj obtained by the high-sensitivity fluorescent-light image use detecting element 306 and outputting said digitized autofluorescent-light image Zj as a two-dimensional image data.

Figure 4:
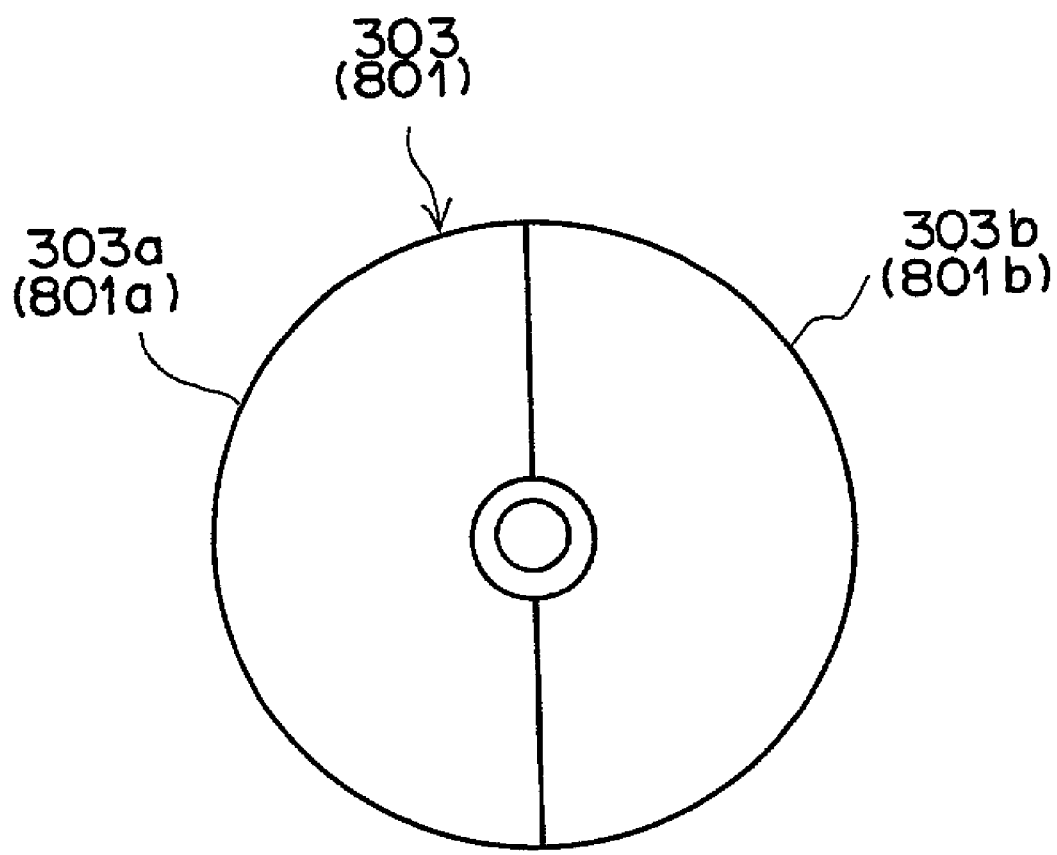
FIG. 4 is a schematic drawing of the optical transmitting filter used in the fist, second, third, and fourth embodiments of a fluorescence endoscope apparatus according to the present invention.

The optical transmitting filter 303, as shown in FIG. 4, is formed of two types of optical filters: an optical filter 303a, which is a band-pass filter for transmitting light in the 430-730 nm wavelength range, and an optical filter 303b, which is a band-pass filter for transmitting light in the 430-470 nm wavelength range.

The image computing unit 400 comprises an image data memory 401 for storing digitized autofluorescent-light images, a standard-values use memory 402 in which a set of standard-value RE have been prerecording for use in determining whether a tissue of which an image has been obtained is a diseased tissue or a normal tissue, an interimage computing portion 403 for computing, based on the ratio between the pixels of each of the two images formed of a different wavelength band stored in the image data memory 401, a computed value for each of said pixels, and for performing a comparison of said computed values for each of said pixels to the prerecorded standard-value RE stored in the standard-values use memory 402 and forming and outputting a computed image according to the results of said comparison.

The standard-values RE are set according to the pixel values of standard autofluorescent-light images of a diseased tissue and a normal tissue obtained in advance.

The display signal processing unit 500 comprises an A/D converter for digitizing a visual-image signal obtained by the normal-image use detecting element 107, a normal-image data memory 502 for storing digitized normal-image signals, and a video signal converting circuit 503 for converting an image signal output from the normal-image memory 502 and the computed image formed by the interimage computing portion 403 to video signals.

The monitor unit 600 comprises a normal-image use monitor 601 and a computed image use monitor 602.

Hereinafter, the operation of a fluorescence endoscope apparatus of the configuration described above implementing the fluorescent-light image obtaining apparatus according to the current embodiment of the present invention will be explained.

First, by use of a displayed normal-image, which has been produced by illuminating-light, for guidance, the endoscope insertion portion 100 is inserted into the body of the patient to the position at which the target tissue 10 of the target area is located. Next, by pressing the foot switch 140, excitation light is caused to be emitted so that a computed image can now be displayed. First, the operation occurring when a normal-image is to be displayed and the operation occurring when a computed image is to be displayed will be explained.

When a computed image is to be displayed, the excitation light use power source 115 is activated based on a signal from the control computer 200 and excitation light Lr having a wavelength of 410 nm is emitted from the GaN semiconductor laser. The excitation light Lr is transmitted by an excitation light use lens 116 and enters the excitation light light guide 101b, and after being guided to the excitation light emitting end of the endoscope insertion portion, is projected onto the target tissue 10 by an illuminating lens 104.

The autofluorescent-light transmitted by the excitation light cutoff filter 302 enters the optical transmitting filter 303. Note that the excitation light cutoff filter 302 is a long-pass cutoff filter transmitting all fluorescent-light of a wavelength of 420 nm or larger. Because the excitation light Lr has a wavelength of 410 nm, the excitation light reflected from the target tissue 10 is cutoff by the excitation light cutoff filter 302 and does not enter the optical transmitting filter 303.

The filter rotating apparatus 304 is activated by the control computer 200, and after being transmitted by the optical transmitting filter 303a or 303b, the fluorescent-light is focused by the fluorescent-light use lens 305 and a fluorescent-light image thereof is obtained by the high-sensitivity fluorescent-light image use detecting element 306; a visible-image signal thereof is input from the to the high-sensitivity fluorescent-light image use detecting element 306 to the A/D converting circuit 307, where it is converted to digital data, and then stored in the image data memory 401.

Computations corresponding to the ratio of each pixel value of each of the images stored in the imaged data memory 401 are performed by the interimage computing portion 403, and a comparison of the computed values obtained thereby and the standard-value RE prerecorded in the standard-values memory 402 is performed and a determination is made as to whether each pixel represents a normal tissue or a diseased tissue, based upon which a computed image is computed and formed. The standard-values RE are set according to the pixel values of standard autofluorescent-light images of a diseased tissue and a normal tissue obtained in advance, and the determination as to whether a tissue is a normal tissue or a diseased tissue is performed so as to determine whether the computed value of each pixel value of each image is large or small relative to the standard-value RE.

The computed image is displayed on the computed-image use monitor 602. By allotting different display colors to a measured zone in which the computed value is smaller than the standard-value RE and a measured zone in which the computed value is larger than the standard-value RE, it is possible for an operator to recognize the comparison results in an instant.

Next, the operation occurring when a normal-image is to be displayed will be explained. When a normal-image is to be displayed, the white-light source power source 112 is activated based on a signal from the control computer 200 and white-light Lw is emitted from the white-light source 111. The white-light Lw enters the white-light light guide 101a via the white-light use focusing lens 113, and after being guided to the excitation light emitting end of the endoscope insertion portion, the white-light Lw is projected onto the target tissue 10 by the illuminating lens 104. The white light Lw reflected from the target tissue 10 is focused by an objective lens 105 and is reflected by a reflection-use prism 108, and is focused on a normal-image use detecting element 107. The visible-image signal from the normal-image use detecting element 107 is input to the A/D converter 501 where it is digitized, after which it is stored in the normal-image data memory 502. The normal-image signal stored by the normal-image data memory 502 is D/A converted by the video signal processing circuit 503, after which it is input to the normal-image use monitor 601 and displayed as a visual image thereon. The continuous operation described above is controlled by the control computer 200.

Then, while a computed image is being displayed, that is, while excitation light is being emitted, when the excitation light emitting end of the endoscope insertion portion 100 comes into contact with the target tissue 10, said contact is detected, and a detection signal indicative thereof is output to the excitation light emission controlling means 120 by way of the detection signal line 131. The excitation light emission controlling means causes the emission of the excitation light to cease upon reception of said detection signal, or sends a signal to the control computer 200 so that the control computer 200 can control the emission of the excitation light so that the excitation light is emitted at an intensity that does not cause injury to the target tissue and ensures for the safety of the patient even when the excitation light emitting end of the endoscope insertion portion and the target tissue are in contact. Afterwards, it is possible to again cause the excitation light to be emitted at image-obtaining intensity by pressing the foot switch 140.

According to a fluorescence endoscope apparatus of the configuration described above and implementing the fluorescent-light image obtaining apparatus according to the present invention, that the excitation light emitting end of the endoscope insertion portion 100 and the target tissue have 10 come into contact is detected, and based on a detection signal indicative thereof, the emission of the excitation light from the excitation light emitting end of the endoscope insertion portion is ceased or controlled so as to be emitted at a safe intensity not causing injury to the target tissue 10, whereby the safety of the patient from the exposure to excessive excitation light can be ensured.

Figure 5:
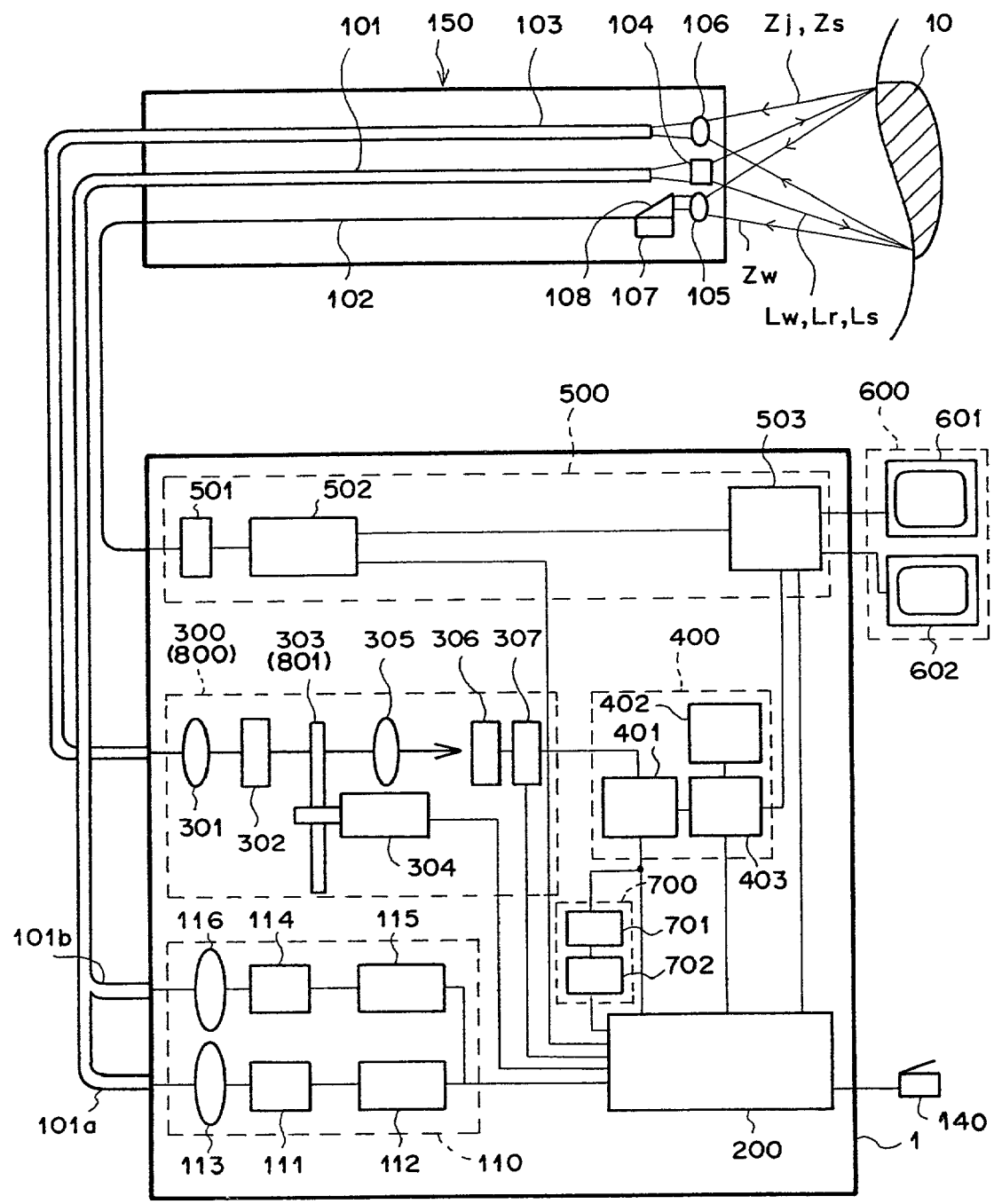
FIG. 5 is a schematic drawing of a fluorescence endoscope apparatus according to the second and third embodiments of the present invention.

Next, the second embodiment of the present invention will be explained. FIG. 5 is a schematic drawing of a fluorescence endoscope apparatus implementing the fluorescent-light image obtaining apparatus according to the present invention. Note that in so far as further explanation of elements that are the same as those of the first embodiment shown in FIG. 3 is not required, it has been omitted.

The fluorescence endoscope apparatus according to the current embodiment excludes the contact detecting means 130 and the detecting line 131 occurring in the first embodiment, and is provided with an excitation light emission controlling unit 700 comprising a distance parameter detecting means 701 for detecting the pixel data of an obtained fluorescent-light image as a parameter correlated to the distance between the endoscope insertion portion 100 and the target tissue 10, and an excitation light emission controlling means 702 for causing, based on said parameter, the emission of the excitation light to cease, or causing the excitation light to be emitted at a safe intensity not causing injury to the target tissue.

Next, the operation of a fluorescence endoscope apparatus of the configuration described above according to the current embodiment of the present invention will be explained.

First, by use of a displayed normal-image, which has been produced by illuminating-light, for guidance, the endoscope insertion portion 100 is inserted into the body of the patient to the position at which the target tissue 10 of the target area is located. Next, by pressing the foot switch 140, excitation light is caused to be emitted so that a computed image can now be displayed. Note that the intensity of the excitation light output when the emission of the excitation light is initiated is of a safe intensity to the patient not causing injury to the target tissue of the target area, regardless of the distance between the excitation light emitting end of the endoscope insertion portion and the target tissue.

Then, while a computed image is being displayed, the pixel data of an obtained fluorescent-light image is detected by the distance parameter detecting means 701. The detection data thereof is output to the excitation light emission controlling means 702, and with regard to this detection data, that is, the data of the size of each pixel value of the fluorescent-light image, the percentage of the entire image or a specified portion of the image occupied by pixels having a value over a predetermined threshold value is computed. Then, when this percentage is above a predetermined threshold value, the emission of the excitation light is ceased, or a signal is output to the control computer 200 so that the control computer 200 can control the emission of the excitation light so that it is emitted at a safe intensity not causing injury to the target tissue 10 when the distance between the excitation light emitting end of the endoscope insertion portion 100 and the target tissue 10 satisfies the aforementioned threshold value conditions. Afterwards, it is possible to again cause the excitation light to be emitted at image-obtaining intensity by pressing the foot switch 140. Other operations are the same as those occurring in the first embodiment.

According to a fluorescence endoscope apparatus of the configuration described above and implementing the fluorescent-light image obtaining apparatus according to the present invention, a parameter correlating the distance between the excitation light emitting end of the endoscope insertion portion 100 and the target tissue have 10 (in the current embodiment, the light strength of a fluorescent-light image) is detected, and based on said detected parameter, the emission of the excitation light from the excitation light emitting end of the endoscope insertion portion is ceased or controlled so as to be emitted at a safe intensity not causing injury to the target tissue 10, whereby the safety of the patient from the exposure to excessive excitation light can be ensured when the distance between the excitation light emitting end of the endoscope insertion portion and the target tissue 10 is extremely close.

Next, the third embodiment of the present invention will be explained. Because the configuration thereof is substantially the same as that of the second embodiment shown in FIGS. 4 and 5, reference numbers have been assigned in FIGS. 4 and 5 only to elements that differ with those of the second embodiment, and the explanation is provided thereof. Note that in so far as further explanation of those elements in common with the second embodiment is not required, it has been omitted.

The fluorescence endoscope apparatus according to the current embodiment utilizes the white-light source 111 of the second embodiment as a reference-light source, and is provided with an image detecting unit 800 which is provided with a optical transmitting filter 801 instead of an optical transmitting filter 303. Because the white-light Lw emitted from the white-light source 111 contains wavelength bands that can be used as reference-light, the white-light source 111 can be used as a reference-light source.

In addition, the optical transmitting filter 801 comprises an optical transmitting filter 801*a* for transmitting a fluorescent-light image, and an optical transmitting filter 801*b* for transmitting an reference-light image: the optical filter 801*a* is a band-pass filter transmitting light having a wavelength in the 430-730 nm range, and the optical transmitting filter 801*b* is a band-pass filter transmitting light having a wavelength in the 750-900 nm range.

Further, the distance parameter detecting means 701 occurring in the second embodiment has been made so as to detect the pixel data of a reflected-light image, which is obtained upon the irradiation of the target tissue by the reference-light, as a parameter correlated to the distance between the excitation light emitting end of the endoscope insertion portion 100 and the target tissue 10.

Next, the operation of a fluorescence endoscope apparatus of the configuration described above according to the current embodiment of the present invention will be explained.

First, by use of a displayed normal-image, which has been produced by illuminating-light, for guidance, the endoscope insertion portion 100 is inserted into the body of the patient to the position at which the target tissue 10 of the target area is located. Next, by pressing the foot switch 140, excitation light is caused to be emitted so that a computed image can now be displayed.

Here, the operation occurring when a computed image, which is based on an autofluorescent-light image and a reference-light image, is to be displayed will be explained. When a computed image is to be displayed, the white-light source power source 112 is activated based on a signal from the control computer 200 and white light Lw is emitted. This white-light Lw contains the reference-light Ls, which has a wavelength within the 750-900 nm wavelength band. The white-light Lw containing the reference light Ls is transmitted by a lens 113 and enters the white-light light guide 101*a*, and after being guided to the excitation light emitting end of the endoscope insertion portion, the white-light Lw containing the reference-light Ls is projected onto the target tissue 10 by the illuminating lens 104.

The reflected-light reflected from the target tissue upon irradiation thereof by the white-light Lw containing the reference-light Ls is focused by the focusing lens 106 and enters the forward end of the image fiber 103, and passes through the image fiber 103 and enters the excitation light cutoff filter 302. The fluorescent-light transmitted by the excitation light cutoff filter 302 enters the optical transmitting filter 801.

The filter rotating apparatus 304 is activated by the control computer 200, and after a reference-light image Zs is transmitted by the optical filter 801*b*, said reference-light image is focused by a fluorescent-light use focusing lens 305 and obtained by the high-sensitivity fluorescent-light image use detecting element 306, and a visible image signal is input from the high-sensitivity fluorescent-light image use detecting element 306 to the A/D converting circuit 307 where it is digitized, after which it is stored in the image data memory 401. Here, only the reference-light image Zs formed of the reflected-light reflected from the target tissue 10 upon irradiation thereof by the white-light Lw containing the reference-light Ls is transmitted by the optical filter 801*b*. Further, the reference-light image data is stored in a memory zone different from that in which the autofluorescent-light image data is stored within the image data memory 401. The operation with respect to an autofluorescent-light image is the same up to the storage thereof in the image data memory 401 as occurred in the first embodiment.

Computations according to the ratio of each of the pixel values of an autofluorescent-light image and a reference-light image stored in the image data memory 401 are performed by the interimage computing portion 403, and the computed values obtained thereby and the standard-value RE prerecorded in the standard-value memory 402 are compared and a determination is made as to whether each pixel represents a normal tissue or a diseased tissue, based upon which a computed image is computed and formed. The standard-values RE are set according to the pixel values of standard autofluorescent-light images of a diseased tissue and a normal tissue obtained in advance.

Then, while a computed image is being displayed, the pixel data of an obtained reflected-light image is detected by the distance parameter detecting means 701. The detection data thereof is output to the excitation light emission controlling means 702, and with regard to this detection data, that is, the data of the size of each pixel value of the reflected-light image, the percentage of the entire image or a specified portion of the image occupied by pixels having a value over a predetermined threshold value is computed. Then, when this percentage is above a predetermined threshold value, the emission of the excitation light is ceased, or a signal is output to the control computer 200 so that the control computer 200 can control the emission of the excitation light so that it is emitted at a safe intensity not causing injury to the target tissue 10 when the distance between the excitation light emitting end of the endoscope insertion portion 100 and the target tissue 10 satisfies the aforementioned threshold value conditions. Afterwards, it is possible to again cause the excitation light to be emitted at image-obtaining intensity by pressing the foot switch 140. Other operations are the same as those occurring in the second embodiment.

Note that according to the embodiment described above, because the white-light source is used as the reference-light source, when the excitation light is controlled so as to be of a predetermined strength, it is desirable that the strength of the reference-light, that is, the strength of the white-light be controlled at the same time. In this case, when a halogen lamp, an Xe lamp, etc. is used as the white-light source 111, the strength of the white-light can be controlled by, for example, controlling a filter or a diaphragm that has been provided between the white-light source 111 and the white-light use lens 113.

According to a fluorescence endoscope apparatus of the configuration described above implementing the fluorescent-light image obtaining apparatus according to the present invention, by utilizing a distance parameter based on a clear reference-light image in order to estimate the distance between the excitation light emitting end of the endoscope insertion portion and the target tissue, in addition to the results obtained in the second embodiment, the emission of the excitation light can be more precisely controlled.

Figure 6:
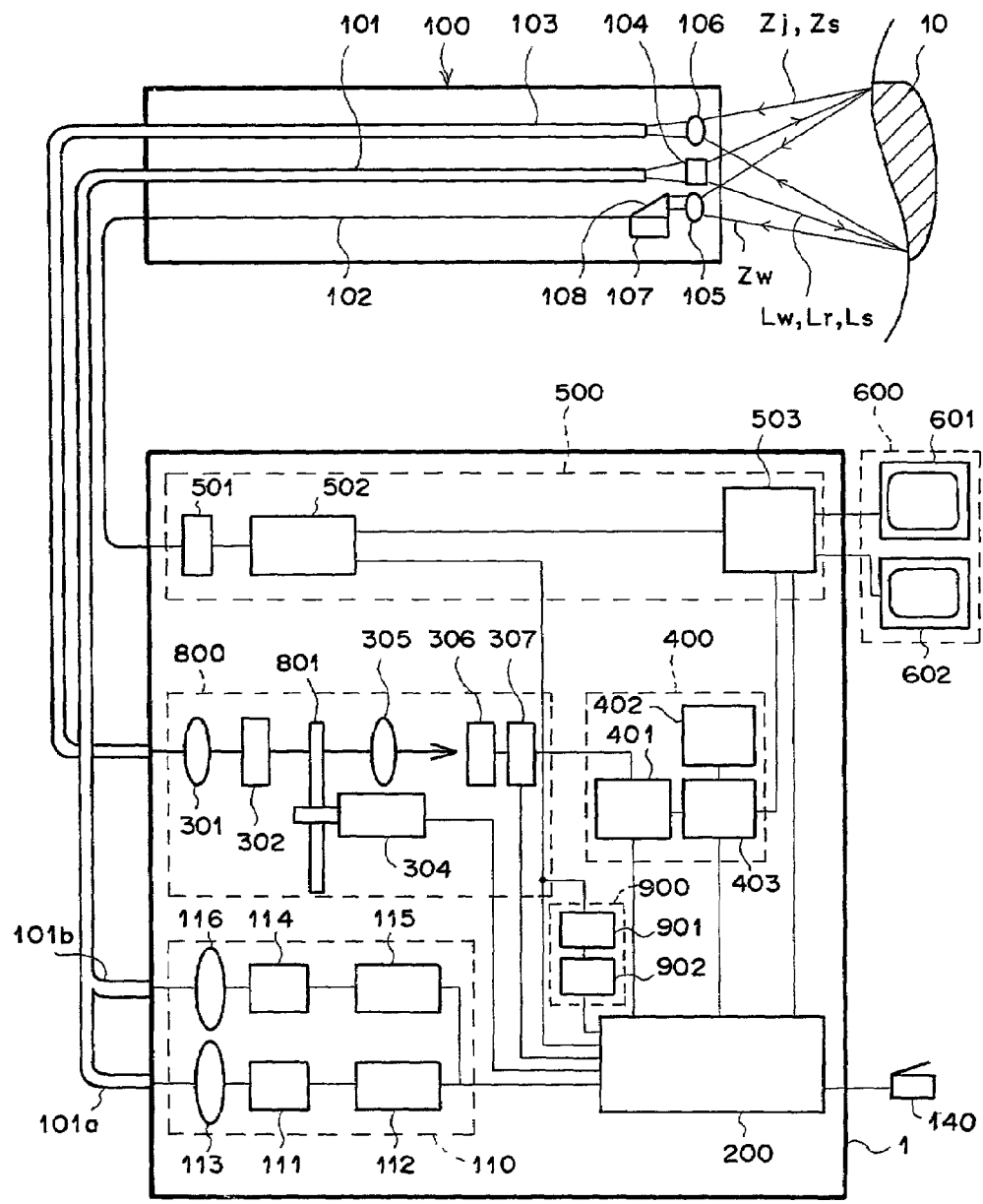
FIG. 6 is a schematic drawing of a fluorescence endoscope apparatus according to the fourth embodiment of the present invention.

Next, the fourth embodiment of the present invention will be explained. FIG. 6 is a schematic drawing of a fluorescence endoscope apparatus implementing the fluorescent-light image obtaining apparatus according to the present invention. Note that in so far as further explanation of elements that are the same as those of the third embodiment is not required, it has been omitted.

According to the fluorescence endoscope apparatus of to the current embodiment, the distance parameter detecting means 701 occurring in the third embodiment has been made so as to detect the pixel data of a normal-image, which is obtained upon the irradiation of the target tissue by the white-light Lw, as a parameter correlated to the distance between the excitation light emitting end of the endoscope insertion portion 100 and the target tissue 10, and is designated as distance parameter detecting device 901. Next, the operation of a fluorescence endoscope apparatus of the configuration described above according to the current embodiment of the present invention will be explained.

First, by use of a displayed normal-image, which has been produced by illuminating-light, for guidance, the endoscope insertion portion 100 is inserted into the body of the patient to the position at which the target tissue 10 of the target area is located. Next, by pressing the foot switch 140, excitation light is caused to be emitted so that a computed image can now displayed.

Then, while a computed image is being displayed, the pixel data of an obtained normal-image is detected by the distance parameter detecting means 901. The detection data thereof is output to the excitation light emission controlling means 902, and with regard to this detection data, that is, the data of the size of each pixel value of the reflected-light image, the percentage of the entire image or a specified portion of the image occupied by pixels having a value over a predetermined threshold value is computed. Then, when this percentage is above a predetermined threshold value, the emission of the excitation light is ceased, or a signal is output to the control computer 200 so that the control computer 200 can control the emission of the excitation light so that it is emitted at a safe intensity not causing injury to the target tissue 10 when the distance between the excitation light emitting end of the endoscope insertion portion 100 and the target tissue 10 satisfies the aforementioned threshold value conditions. Afterwards, it is possible to again cause the excitation light to be emitted at image-obtaining intensity by pressing the foot switch 140. Other operations are the same as those occurring in the third embodiment.

According to a fluorescence endoscope apparatus of the configuration described above implementing the fluorescent-light image obtaining apparatus according to the present invention, the same results obtained in the third embodiment can be obtained.

In addition, according to each of the embodiments of the present invention described above, control of the emission of the excitation light can be performed by controlling the direct current in the semiconductor-laser use power source. By employing this current-control method to control the emission of the excitation light, the configuration of the apparatus can be simplified. Further, by employing a direct current modulating method of high-responsivity, safety can be ensured when the subject has come too close, and also, the operability and performance can be improved as the excitation light is capable of being rapidly restored to original strength when the subject is located again at an appropriate distance.

Further, a mercury lamp, etc., and not a semiconductor laser can be used as the excitation light source; in this case, control of the emission of the excitation light can be performed by, for example, controlling a filter or a diaphragm that has been provided between the excitation light source and the excitation light use lens.

Figure 7:
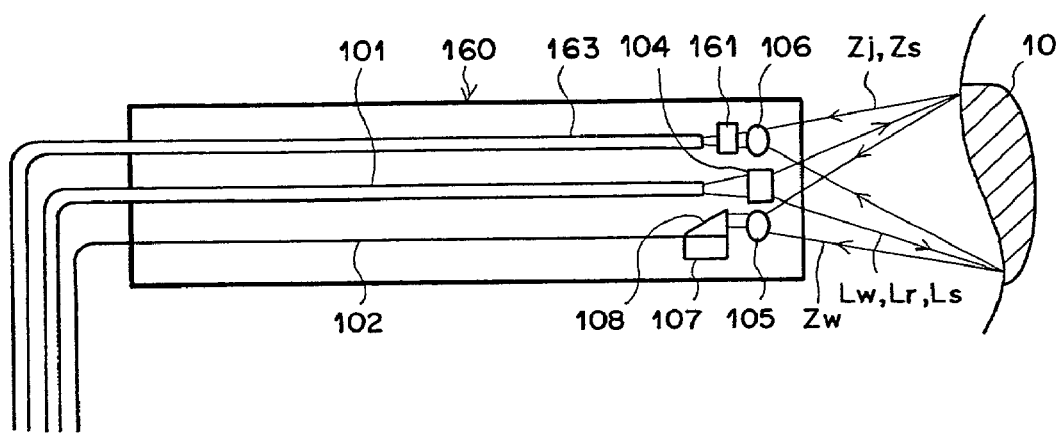
FIG. 7 is a schematic drawing of the endoscope insertion portion, for cases in which the image fiber is a composite glass fiber, used in the first, second, third, and fourth embodiments of a fluorescence endoscope apparatus according to the present invention.

Additionally, in each of the above described embodiments of the present invention, the image fiber 163 can be a composite glass fiber instead of a silicon fiber. In this case, because fluorescent-light is emitted from a composite glass fiber upon the introduction thereto of the excitation light, the excitation light cutoff filter shown in FIG. 7 (the contact detecting means and the detection signal line occurring in the first embodiment are not shown) must be disposed between the focusing lens 106 and the autofluorescent-light image input face of the image fiber 163, and not within the image signal processing portion. By using a composite glass fiber instead of a silicon fiber, the cost can be reduced.

Further, the fluorescent-light image obtaining apparatus according to the present invention can be applied for detecting the fluorescent-light emitted from a target tissue, which has absorbed a fluorescence diagnosing drug beforehand, upon the irradiation thereof by an excitation light.

Still further, the fluorescent-light image obtaining apparatus according to the present invention can be implemented in a colposcope or a laparoscope utilizing the fluorescent-light emitted due to the irradiation of an excitation light.

What is claimed is:

1. A fluorescent-light image obtaining apparatus comprising
    excitation light emitting means for projecting excitation light onto a target tissue, and
    illuminating light emitting means for projecting illuminating light onto the target tissue, and
    fluorescent-light image obtaining means for obtaining a fluorescent-light image formed of the fluorescent-light emitted from the target tissue upon irradiation thereof by the excitation light, and
    a normal-image obtaining means for obtaining a normal-image formed of the illuminating light reflected from the target tissue upon irradiation thereof by the illuminating light, further comprising
    a contact detecting means for detecting that the distal end of excitation light emitting means has come into contact with the target tissue, and
    an excitation light emission controlling means for controlling, in response to the detection signal of said contact detecting means, the output of the excitation light emitted from the excitation light emitting means.

2. A fluorescent-light image obtaining apparatus as defined in claim 1, wherein
    the excitation light emission control means is a current controlling means for controlling the current occurring in the excitation light source.

3. A fluorescent-light image obtaining apparatus as defined in claim 1, wherein
    said excitation light emission controlling means causes the emission of the excitation light from the excitation light emitting means to stop.

4. A fluorescent-light image obtaining apparatus as defined in claim 1, wherein
    said excitation light emission controlling means causes the excitation light from the excitation light emitting means to be emitted at an intensity below a predetermined value.

5. A fluorescent-light image obtaining apparatus comprising
    excitation light emitting means for projecting excitation light onto a target tissue, and
    illuminating light emitting means for projecting illuminating light onto the target tissue, and
    fluorescent-light image obtaining means for obtaining a fluorescent-light image formed of the fluorescent-light emitted from the target tissue upon irradiation thereof by the excitation light, and
    a normal-image obtaining means for obtaining a normal-image formed of the illuminating light reflected from the target tissue upon irradiation thereof by the illuminating light, further comprising
    a distance parameter detecting means for detecting a parameter correlating the distance between the distal end of excitation light emitting means and the target tissue, and
    an excitation light emission controlling means for controlling, based on the parameter detected by the distance parameter detecting means, the output of the excitation light emitted from the excitation light emitting means.

6. A fluorescent-light image obtaining apparatus as defined in claim 5, wherein the parameter is based on the light intensity of the fluorescent-light image obtained by the fluorescent-light image obtaining means.

7. A fluorescent-light image obtaining apparatus as defined in claim 6, wherein the parameter is based on the pixel values of the entire image or a predetermined portion of a fluorescent-light image obtained by the fluorescent-light image obtaining means.

8. A fluorescent-light image obtaining apparatus as defined in claim 5, wherein the parameter is the light intensity of the normal-image obtained by the normal-image obtaining means.

9. A fluorescent-light image obtaining apparatus as defined in claim 8, wherein the parameter is based on the pixel values of the entire image or a predetermined portion of a normal-image obtained by the normal-image obtaining means.

10. A fluorescent-light image obtaining apparatus as defined in claim 5, further comprising reference-light emitting means for projecting a reference-light onto the target tissue, and reflected-light image obtaining means for obtaining a reflected-light image reflected from the target tissue upon irradiation thereof by the reference-light, wherein said parameter is based on the light intensity of the reflected-light image obtained by the reflected-light image obtaining means.

11. A fluorescent-light image obtaining apparatus as defined in claim 10, wherein the parameter is based on the pixel values of the entire image or a predetermined portion of a reflected-light image obtained by the reflected-light image obtaining means.

12. A fluorescent-light image obtaining apparatus as defined in claim 5, wherein the excitation light emission control means is a current controlling means for controlling the current occurring in the excitation light source.

13. A fluorescent-light image obtaining apparatus as defined in claim 5, wherein said excitation light emission controlling means causes the emission of the excitation light from the excitation light emitting means to stop.

14. A fluorescent-light image obtaining apparatus as defined in claim 5, wherein said excitation light emission controlling means causes the excitation light from the excitation light emitting means to be emitted at an intensity below a predetermined value.

15. The fluorescent-light image obtaining apparatus as defined in claim 1, wherein a strength of the excitation light is controlled at the same time as the strength of the illuminating light.

16. The fluorescent-light image obtaining apparatus as defined in claim 5, wherein a strength of the excitation light is controlled at the same time as the strength of the illuminating light.

17. The apparatus of claim 1, wherein the contact detecting means is attached to the distal end of the excitation light emitting means for imaging the target tissue and emits a signal to the light emission controlling means upon contact with the target tissue.

\* \* \* \* \*